United States Patent
Urushiya

(10) Patent No.: US 7,145,979 B2
(45) Date of Patent: Dec. 5, 2006

(54) X-RAY CT IMAGE TAKING APPARATUS AND X-RAY CT IMAGE TAKING METHOD

(75) Inventor: Hiroyuki Urushiya, Saitama-ken (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/140,898

(22) Filed: Jun. 1, 2005

(65) Prior Publication Data

US 2005/0276371 A1    Dec. 15, 2005

(30) Foreign Application Priority Data

Jun. 15, 2004    (JP)    ............................. 2004-177404

(51) Int. Cl.
*G01N 23/083*    (2006.01)
(52) U.S. Cl. ............................. 378/4; 378/15; 378/901
(58) Field of Classification Search .................... 378/4, 378/8, 15, 901
See application file for complete search history.

(56) References Cited

U.S. PATENT DOCUMENTS

| | | | | |
|---|---|---|---|---|
| 5,270,923 A | * | 12/1993 | King et al. | 382/131 |
| 5,671,263 A | * | 9/1997 | Lai | 378/8 |
| 5,708,690 A | * | 1/1998 | Hsieh | 378/4 |
| 5,960,056 A | * | 9/1999 | Lai | 378/4 |
| 5,991,356 A | * | 11/1999 | Horiuchi et al. | 378/8 |
| 6,108,575 A | * | 8/2000 | Besson | 600/425 |
| 6,324,247 B1 | * | 11/2001 | Besson | 378/15 |
| 6,907,100 B1 | * | 6/2005 | Taguchi | 378/4 |

2002/0025017 A1    2/2002    Stergiopoulos et al. ........ 378/8

FOREIGN PATENT DOCUMENTS

| | | |
|---|---|---|
| EP | 0 430 549 A2 | 6/1991 |
| WO | WO 2004/010383 A2 | 1/2004 |

OTHER PUBLICATIONS

Wesarg, S., et al., " Parker Weights Revisited," Medical Physics, American Institute of Physics, New York, USA, vol. 29, No. 3 (Mar. 2002), pp. 372-378, XP012011740, ISSN: 0094-2405.

* cited by examiner

*Primary Examiner*—Allen C. Ho
(74) *Attorney, Agent, or Firm*—Fitzpatrick, Cella, Harper & Scinto

(57) ABSTRACT

To obtain a tomographic image suffering little from artifact and the determination of the quality of image.

(1) Step 1: With the axis of abscissas as the fan angle or channel direction of an X-ray detector and the axis of ordinates as the projection angle direction of an X-ray source 11, projection data are arranged side by side to thereby prepare a sinogram.

(2) Step 2: from the sinogram, the projection data of an opposite fan beam is prepared at each projection angle.

(3) Step 3: the degree of consistency with the projection data of the opposite fan beam is obtained at each projection angle.

(4) Step 4: The region of reference error of the degree of consistency is obtained, and a projection angle region is determined from this region of reference error.

(5) Step 5: the projection data in the projection angle region obtained at the step 4 is reconstructed to thereby prepare a tomographic image.

7 Claims, 8 Drawing Sheets

X-RAY CT IMAGE TAKING APPARATUS AND X-RAY CT IMAGE TAKING METHOD

BACKGROUND OF THE INVENTION

1. Field of the Invention

This invention relates to an X-ray CT apparatus for reconstructing a tomographic image by the use of projection data.

2. Related Background Art

In an X-ray CT (computer tomography) apparatus, there is practiced half scan reconstruction which reconstructs an image by the use of projection data of 180 degrees+fan angle without the use of projection data corresponding to one full rotation. Further, it is also known that when use is made of projection data of 180 degrees+fan angle to 360 degrees, reconstruction can be done by a similar method as disclosed in Japanese Patent Application Laid-Open No. 2001-299738.

Describing this by the use of sinogram, in a system construction by an X-ray detector 2 opposed to an X-ray source 1 shown in FIG. 9 of the accompanying drawings with a subject S interposed therebetween, a sinogram is an image formed by projection data arranged with the fan angle or channel direction of the X-ray detector 2 as the axis of abscissas and the projection angle direction of the X-ray source 1 as the axis of ordinates, as shown in FIG. 10 of the accompanying drawings. Herein, description is made with respect to an arcuate X-ray detector 2 and therefore, the axis of abscissas is the fan angle, but in the case of a linear X-ray detector 2, conversion from distance to angle is necessary.

In a case where a fan beam is used as the X-ray source 1, as shown in FIG. 11 of the accompanying drawings, an X-ray transmission route of a fan angle $\alpha$ coincides with an X-ray transmission route of which the fan angle is $-\alpha$ when a projection angle is rotated by 180 degrees $+2\alpha$. This means that assuming that the transmission data value of a transmission route of a fan angle $\alpha$ and a projection angle $\beta$ is $g(\alpha,\beta)$, the transmission data value $g(-\alpha,\Pi+\beta+2\alpha)$ of a transmission route opposed thereto coincides therewith. That is, $g(\alpha,\beta)=g(-\alpha,\Pi+\beta+2\alpha)$. This is represented on the sinogram as shown in FIG. 12 of the accompanying drawings.

Thereby, it will be seen that when the projection angle is 0 degree to 180 degrees $+2\delta$ ($\delta$ being the one side maximum angle of the fan), a gray portion shown in FIG. 13 of the accompanying drawings is dually overlapping data. Thus, if this overlapping data portion is corrected by a weighting factor so as to become the same weight as a non-duplicate portion, it can be normally reconstructed.

Even in the case of a projection angle greater than 180 degrees+fan angle $\alpha$, reconstruction can be accomplished by the use of a weighting factor as in half scan reconstruction.

The reconstruction used in the actual CT system is either full scan reconstruction using projection data fully 360 degrees or half scan reconstruction using projection data of 180 degrees+fan angle $\alpha$. In the case of the half scan reconstruction, projection data used for the reconstruction is substantially a half and therefore, the quality of image is insufficient.

Also, in the case of full scan reconstruction, projection data used becomes double and correspondingly, the time required for image taking becomes double, and the risk of an inconvenience such as, for example, body movement or the fluctuation of the quality of X-ray occurring during scanning becomes high, and if such inconvenience occurs, a construction may occur to the projection data and in some cases, an artifact may occur or the deterioration of the quality of image may occur.

Reconstruction in a case when use is made of projection data of a 0 degree–180 degrees+fan angle $\alpha$ to 360 degrees is also known, but no consideration is given to what range of projection data should be used.

SUMMARY OF THE INVENTION

The present invention has been made in view of the above-noted problems and provides a technique relating to an X-ray CT apparatus which reduces the influence of body movement, the fluctuation of the quality of X-ray or the like upon image taking.

In order to solve the above-noted problems, an X-ray CT image taking apparatus for obtaining a reconstructed image from projection data obtained from X-ray image taking which is one aspect of the present invention is characterized by the provision of:

calculation means for obtaining the degree of consistency of projection data opposed to the projection data of a projection angle at each projection angle;

determination means for determining the effective region of the projection angle by the use of the degree of consistency obtained by the calculation means; and tomographic image forming means for reconstructing an image by the use of the projection data within the effective region determined by the determination means to thereby obtain a tomographic image.

Other features and advantages of the present invention will become apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, an illustrate embodiment of the invention and, together with the description, serve to explain the principles of the invention.

DESCRIPTION OF THE PREFERRED EMBODIMENTS

Preferred embodiment of the present invention will hereinafter be described in detail in accordance with the accompanying drawings.

The present invention will now be described in detail with respect to the shown embodiments thereof.

Figure 1:
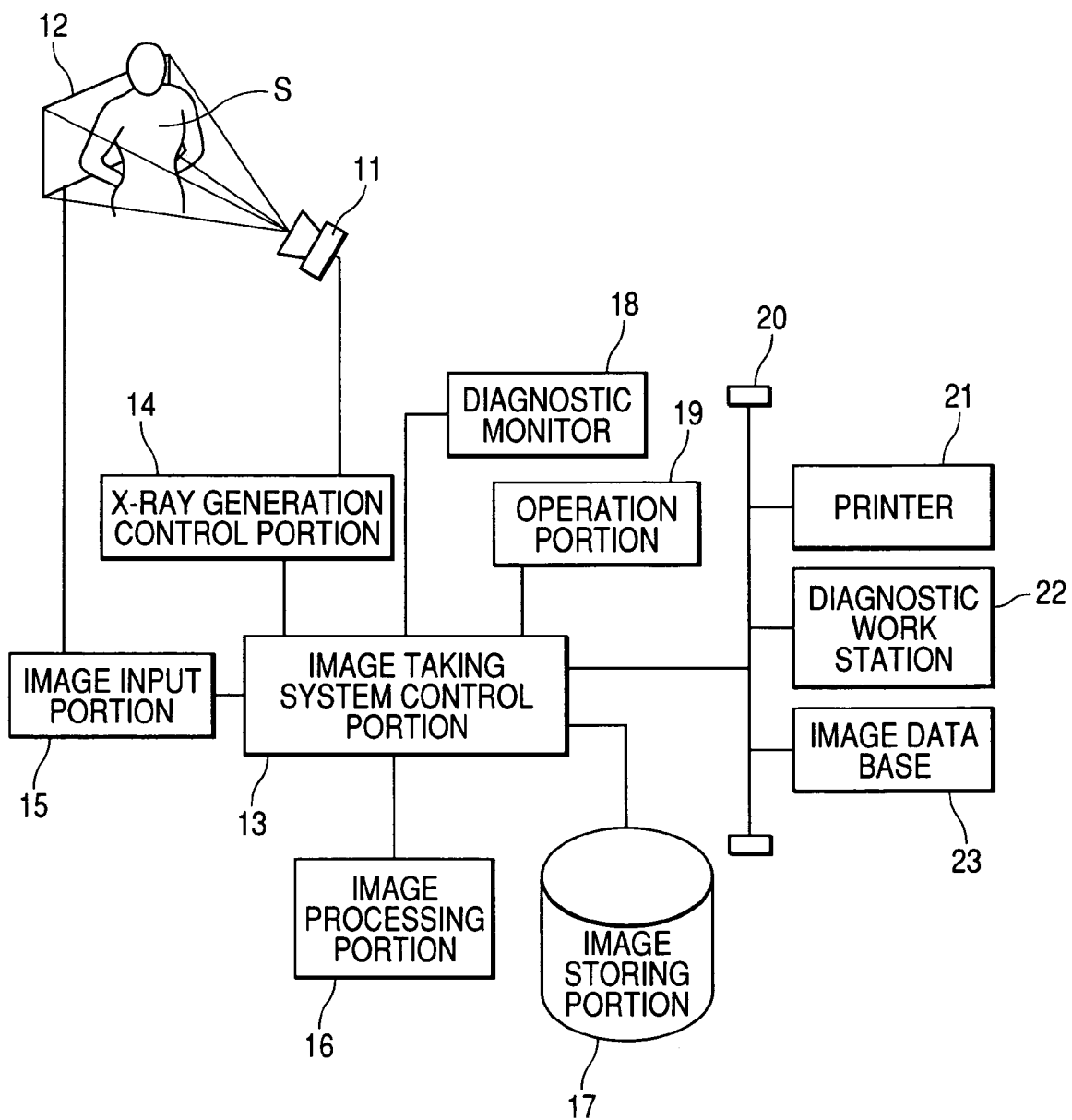
FIG. 1 shows the construction of an X-ray CT system according to an embodiment of the present invention.

FIG. 1 shows the construction of an X-ray CT system according to Embodiment 1. An X-ray source 11 and an X-ray detector 12 are disposed with a subject S which is a patient interposed therebetween, and the output of an image taking system control portion 13 is connected to the X-ray source 11 through an X-ray generation control portion 14. Also, the output of the X-ray detector 12 is connected to the image taking system control portion 13 through an image input portion 15. Further, an image processing portion 16, an image storing portion 17, a diagnostic monitor 18, an operation portion 19 and a network 20 are connected to the image taking system control portion 13, and a printer 21, a diagnostic work station 22 and an image data base 23 are connected to the network 20.

An X-ray generated from the X-ray source 11 controlled by the X-ray generation control portion 14 is transmitted through the subject S which is a patient and is detected by the X-ray detector 12, and the detected X-ray is inputted as a projection image to the image input portion 15 through the image taking system control portion 13. The X-ray source 11 and the X-ray detector 12 effect the collection of the projection image at each rotation angle while effecting rotation with the subject S as a rotation center. Alternatively, a subject S fixed onto a rotary table may be rotated while the positional relationship between the X-ray source 11 and the X-ray detector 12 is kept.

The inputted projection image of each rotational angle is subjected to image processing such as the correction of the X-ray detector 12, anti-processing including logarithmic conversion and reconstruction processing by the image processing portion 16, and a tomographic image group is prepared. The prepared tomographic image group is displayed on the diagnostic monitor 18, is stored in the image storing portion 17, or is outputted to the printer 21, the diagnostic work station 22 and the image data base 23 through the network 20. Various operations such as a window operation for display, the changeover display operation of a tomographic image in a body axis direction, a cross-section converting operation and a three-dimensional surface display operation are performed by the operation portion 19.

Figure 2:
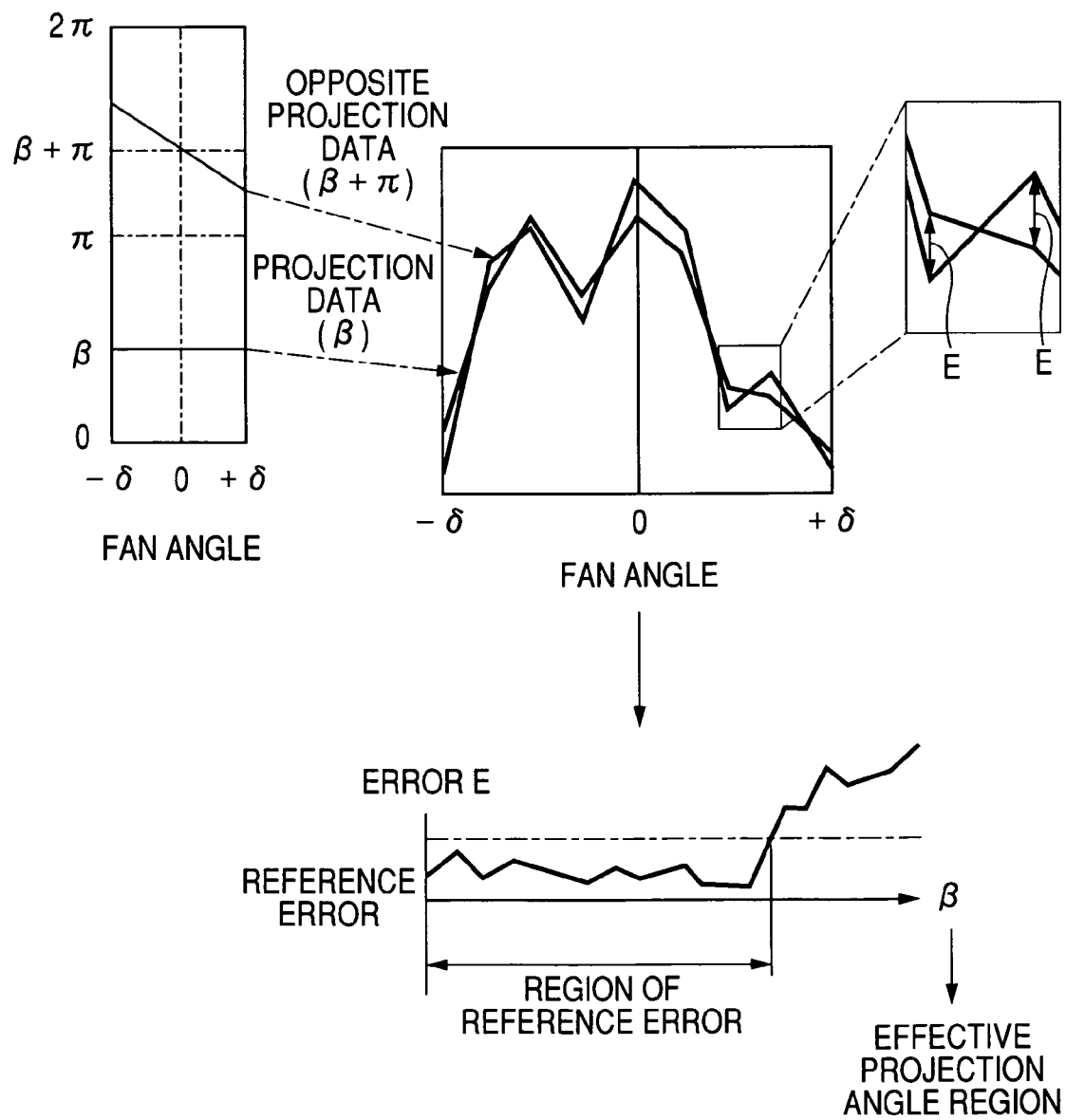
FIG. 2 is an illustration for obtaining the region of reference error of a projection angle from sinogram.

FIG. 2 shows an illustration of the operation in this system, and the error of opposite fan beams with respect to projection data, i.e., the degree of consistency, is obtained for each projection angle from a sinogram, and a region in which this greess of consistency is within the reference is obtained, and an effective projection angle region is determined therefrom, and reconstruction is effected by the use of projection data in this region of reference error.

In order to carry out this, the procedure of the steps in the following items (1) to (5).

(1) Step 1: a sinogram is prepared.

Figure 10:
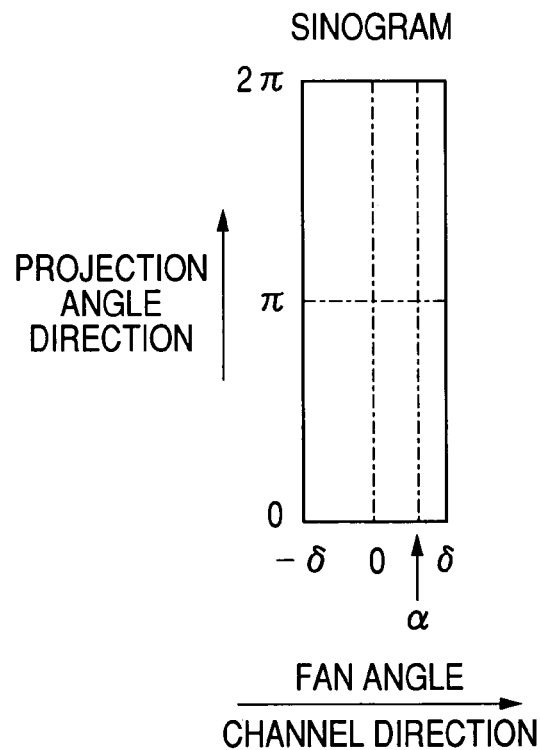
FIG. 10 is an illustration of the sinogram.

The sinogram, as shown in FIG. 10, is an image in which projection data are arranged with the axis of abscissas as the fan angle $\alpha$ or channel direction of the X-ray detector 12, and the axis of ordinates as the projection angle direction of the X-ray source 11.

When a two-dimensional plane detector is used as the X-ray detector 12, a detector row of a particular position is used in the body axis direction. This particular position can be, for example, a position coincident with the center axis of an X-ray beam.

Alternatively, sinograms may be prepared at a plurality of positions and up to a step 4 may be executed, and an effective projection angle common at all the positions may be determined as an effective projection angle.

(2) Step 2: the projection data of the opposite fan beams is prepared for each projection angle from the sinogram.

Figure 11:
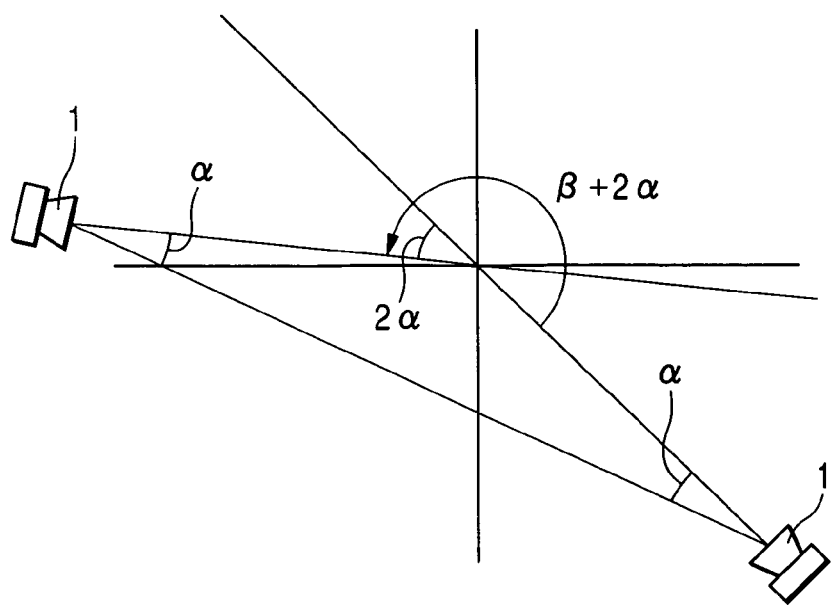
FIG. 11 is an illustration of opposite projection data.
Figure 12:
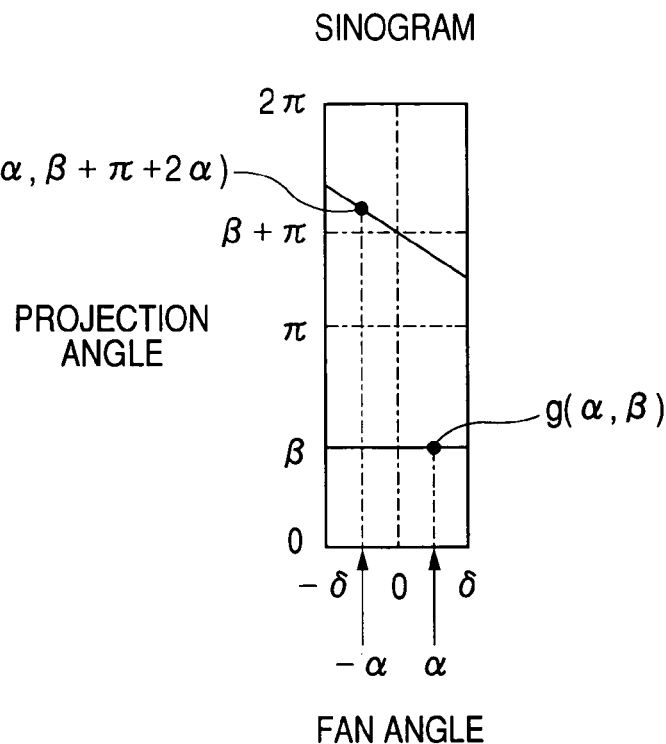
FIG. 12 is an illustration of the opposite projection data by a sinogram.
Figure 13:
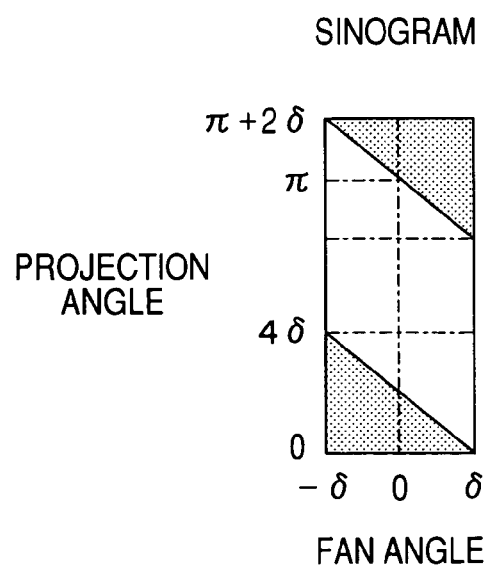
FIG. 13 is an illustration of overlapping projection data by a sinogram.

In a case where a fan beam is used as the X-ray Source 11, when the projection angle is rotated by 180 degrees +2$\alpha$, as shown in FIG. 11, the X-ray transmission route of a fan angle $\alpha$ coincides with an X-ray transmission route of which the fan angle is $-\alpha$. As illusted in FIG. 12, the transmission value $g(\alpha,\beta)$ of the transmission route is coincident with $g(-\alpha,\Pi+\beta+2\alpha)$ and the data of $g(-\alpha,\Pi+\beta+2\alpha)$ has its projection angle digitized and therefore, actually the projection data does not always exist on $\Pi+\beta+2\alpha$. In that case, projection data is prepared from the preceding and succeeding projection data by interpolation. The $g(\alpha,\beta)$ and $g(-\alpha,\Pi+\beta+2\alpha)$ can be represented as one-dimensional vector data at each digitized projection angle $\beta i$.

These one-dimensional vector data are set as $g\beta_i(\alpha_j)$ and $[g\beta_i(\alpha_j)]$, respectively. Here, $\alpha_j$ and $[\alpha_j]$ correspond to each other and $\beta_i$ and $[\beta_i]$ correspond to each other, and these $g\beta_i(\alpha_j)$ and $[g\beta_i(\alpha_j)]$ are data which should originally coincide with each other.

(3) Step 3: the degree of consistency of the opposite fan beams with the projection data is obtained for each projection angle.

This degree of consistency refers to the degree of coincidence between $g\beta_i(\alpha_j)$ and $[g\beta_i(\alpha_j)]$. That is, the degree of coincidence between $g\beta_i(\alpha_j)$ and $[g\beta_i(\alpha_j)]$ being high means that the error between $g\beta_i(\alpha_j)$ and $[g\beta_i(\alpha_j)]$ is small.

So, as an index of the degree of consistency, use can be made of the average square error E of $g\beta_i(\alpha_j)$ and $[g\beta_i(\alpha_j)]$. This can be obtained by varying j by the expression that $E=\sqrt{\Sigma\{g\beta_i(\alpha_j)-[g\beta_i(\alpha_j)]\}^2}$. Of course, the square root need not be obtained, but simply use may be made of an absolute value error $E=|\Sigma\{g\beta_i(\alpha_j)-[g\beta_i(\alpha_j)]\}|$. The smaller are the average square error and the absolute value error E, the higher becomes the degree of consistency.

(4) Step 4: the region of reference error of the degree of consistency is obtained, and the projection angle region is determined from this region of reference error.

Figure 3:
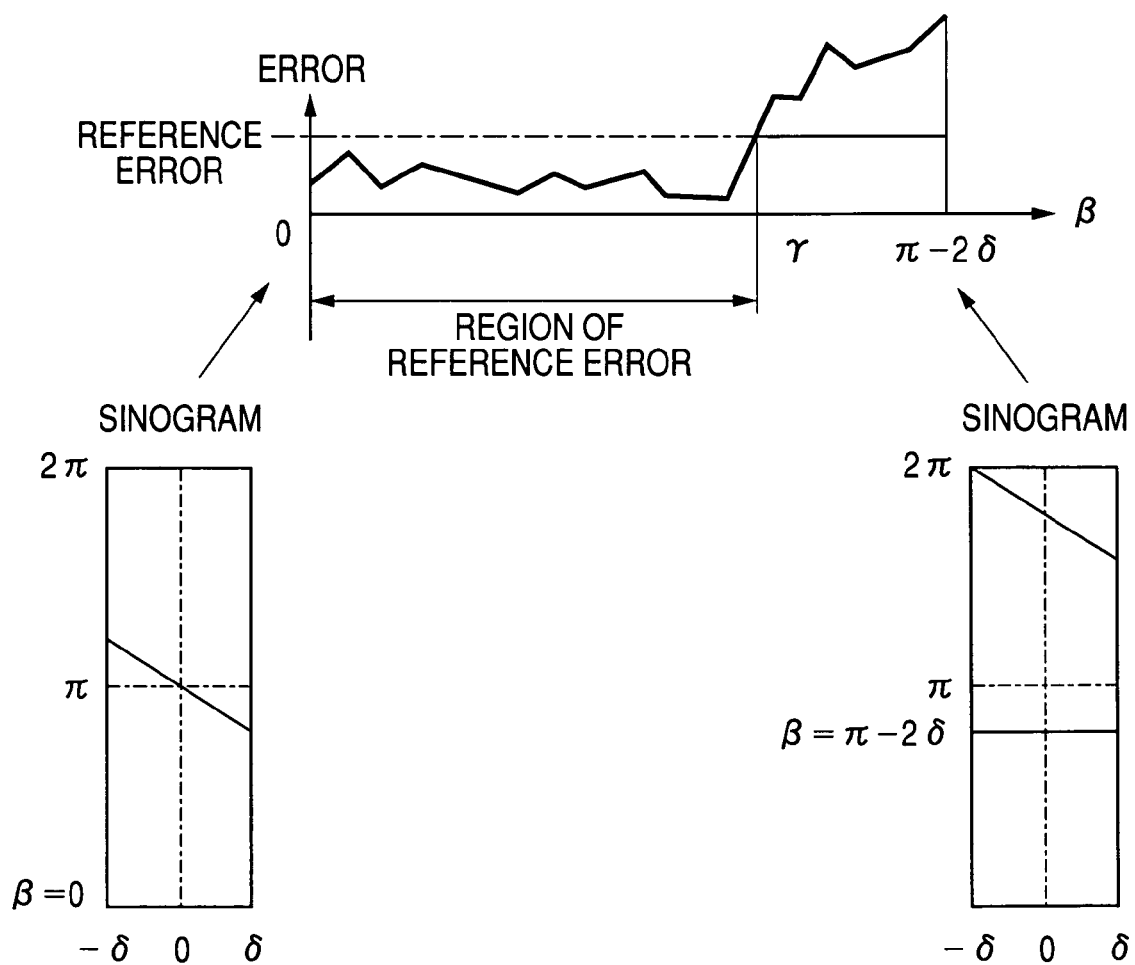
FIG. 3 is an illustration for obtaining the region of reference error of projection data.

The absolute value error E obtained at the step 3 is a one-dimensional vector with $\beta_i$ or $[\beta_i]$ as an index. FIG. 3 shows the absolute value error E obtained from two sinograms, and the axis of abscissas represents the projection angle, and when the fan angle is defined as $\delta$, it can be prepared in a region of 0 to $\Pi-2\delta$. A region in which the absolute value error E of the axis of ordinates is smaller than a predetermined reference error is obtained and is defined as a region of reference error.

Figure 4A:
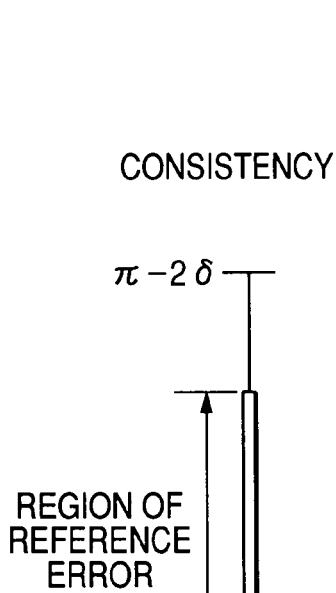
FIGS. 4A and 4B are illustrations for obtaining an effective projection angle region from the region of reference error.
Figure 4B:
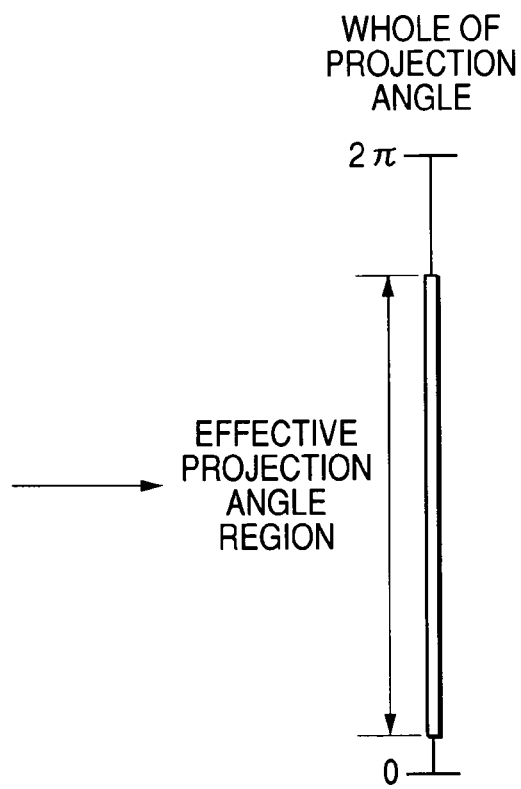

Next, the effective projection angle region of FIG. 4B which can be regarded as normal image taking having been effected is determined from the region of reference error of FIG. 4A.

Figure 5:
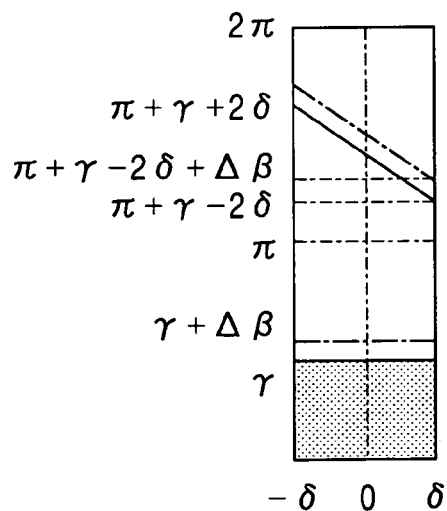
FIG. 5 is an illustration by the sinogram of a projection angle in which there has been a change.

Here, assuming that as shown, for example, in FIG. 3, the region of reference error has been obtained as 0–$\gamma$, at this time, as shown in FIG. 5, $g_\gamma$ and $g_{\gamma+\Pi}$ can be regarded as being coincident with each other up to 0–$\gamma$, and in $\gamma+\Delta\beta$ and thereafter, they can be regarded as being not coincident with each other at all angles. This leads to the presumption that there has been a change in body movement or the like at a point whereat shift occurs from γ to γ+Δβ or from γ+Π to γ+Δβ+Π.

Here, assuming that γ+Π exceeds γ+2δ and there has been a change at the point whereat shift occurs from γ to γ+Δβ, incoincidence occurs before γ and therefore, it can be presumed that the change has occurred not at the point whereat shift occurs from γ to γ+Δβ, but at the point at which shift occurs from δ+Π to δ+Δβ+Π.

Figure 6:
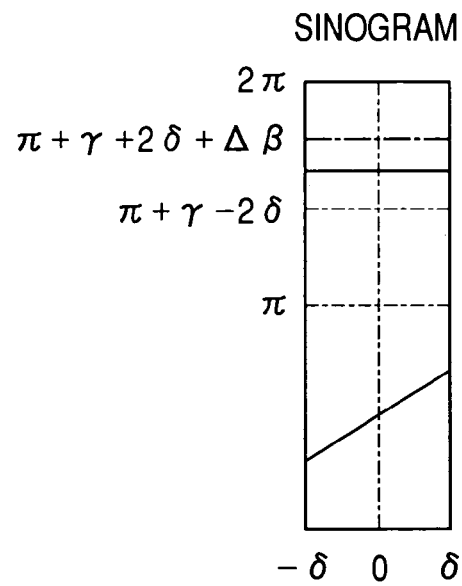
FIG. 6 is an illustration by the sinogram of the effective projection angle region.

However, the point at which shift occurs from γ+Π to γ+Δβ+Π has a width of 4δ as actual projection data and cannot be intactly identified and therefore, as shown in FIG. 6, the degree of consistency of the projection data in the region of γ+Π−2δ to γ+Π+2δ+Δβ and projection data opposite thereto is evaluated as previously described, whereby an effective projection angle region can be determined.

Also when γ+Π has not exceeded Π+2δ, the degree of consistency by the projection data in the region of γ+Π−2δ to γ+Π+2δ+Δβ and the projection data opposite thereto is likewise evaluated, whereby effective projection angle region can be determined.

Figure 7A:
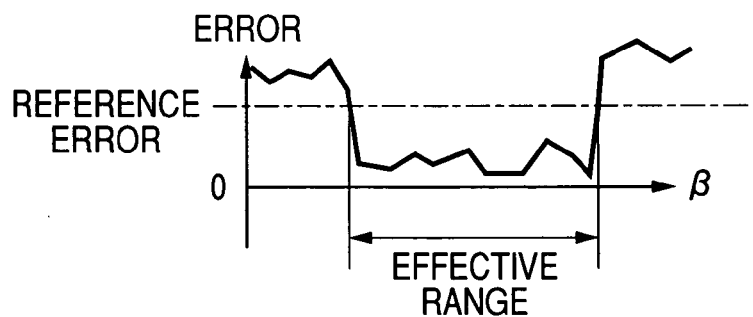
FIGS. 7A and 7B are illustrations of the pattern of an effective region.
Figure 7B:
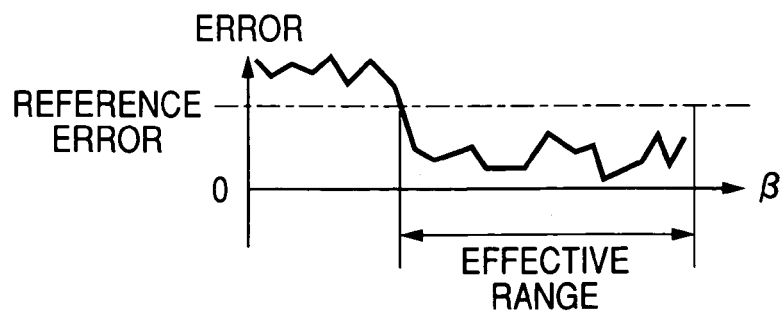

However, if the effective region of the projection angle determined here is smaller than Π+2δ, it means that the projection data necessary for reconstruction are not complete, and image taking can be regarded as having failed. If this judgment is effected at real time in parallel with image taking, it will be possible to discontinue the image taking and prevent excess X-ray exposure at the point whereat the image taking has been judged to have failed. Such judgment can likewise be applied to a case where the effective region is of such a pattern as shown in FIG. 7A and FIG. 7B.

Figure 8:
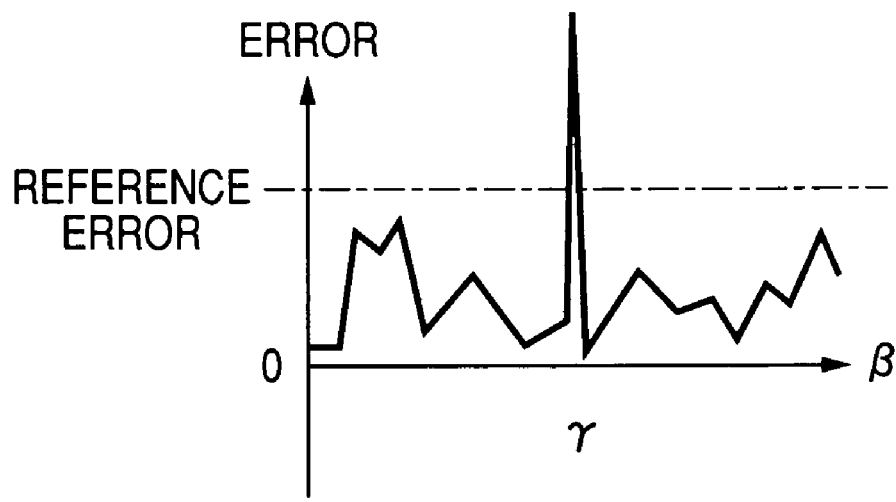
FIG. 8 is an illustration of the pattern of an effective region.
Figure 9:
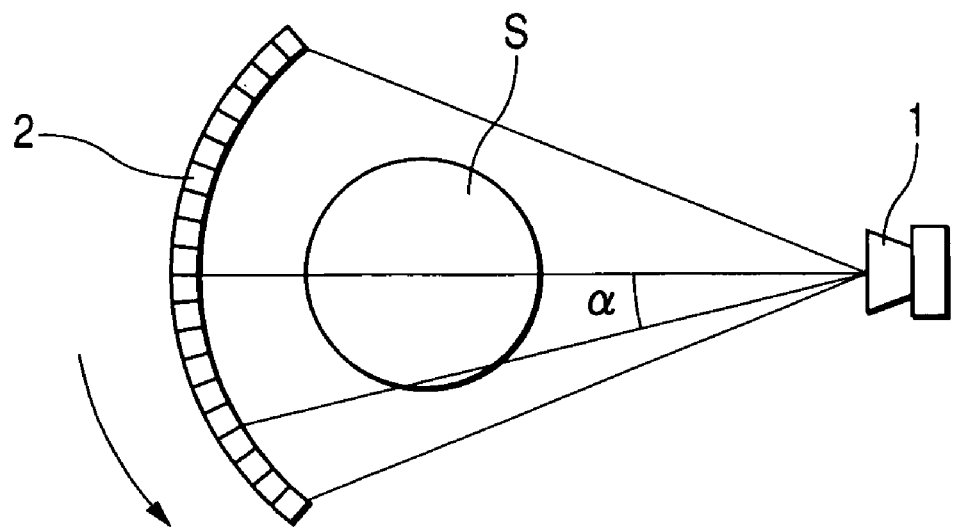
FIG. 9 shows the construction of the X-ray CT system.

In the case of a pattern as shown in FIG. 8 wherein $g_\gamma$ and $g_{\gamma+\Pi}$ are not coincident only at a certain projection angle γ, it can be judged that abnormality is present in the data of the projection angle γ, and projection angles except the projection angle γ can be used as the effective region of the projection angle. In the other cases, the effective region can be considered in a combination of FIGS. 7 and 8.

(5) Step 5: the projection data in the projection angle region obtained at the step 4 is reconstructed to thereby prepare a tomographic image.

The tomographic image can be reconstructed if in principle, there is projection data of 180 degrees+fan angle or greater. In a case of a method when use is made of projection data of 180 degrees+fan angle to 360 degrees, and in 360 degrees scanning, all projection angle data overlap one another, but when reconstruction is to be effected by the use of projection data of less than 360 degrees, there are overlapping projection angles and non-overlapping projection angles and therefore, if the weight of the overlapping projection data is adjusted, normal reconstruction will be possible.

In this manner, there can be prepared a tomographic image using projection data in a normally scanned region.

As described above, according to each embodiment, use is made of projection data in the effective region and therefore, there can be provided a technique regarding an X-ray CT apparatus which reduceds the influence of body movement, the fluctuation or the like of the quality of X-ray upon image taking.

As many apparently widely different embodiments of the present invention can be made without departing from the spirit and scope thereof, it is to be understood that the invention is not limited to the specific embodiment thereof except as defined in the appended claims.

This application claims priority from Japanese Patent Application No. 2004-177404 filed Jun. 15, 2004, which is hereby incorporated by reference herein.

What is claimed is:

1. An X-ray CT image taking apparatus for obtaining a reconstructed image from projection data obtained by X-ray image taking, provided with:

calculation means for obtaining the degree of consistency of projection data opposite to the projection data of a projection angle at each projection angle;

determination means for determining the effective region of said projection angle by the use of said degree of consistency obtained by said calculation means; and tomographic image forming means for reconstructing an image by the use of said projection data in said effective region determined by said determination means to thereby obtain a tomographic image.

2. An X-ray CT image taking apparatus according to claim 1, wherein said degree of consistency has an error between said projection data and said opposite projection data as an evaluated amount.

3. An X-ray CT image taking apparatus according to claim 1, wherein said opposite projection data is obtained by being prepared by interpolation.

4. An X-ray CT image taking apparatus according to claim 1, wherein the determination of said effective region is effected by obtaining a region in which the degree of consistency of said projection data opposite to said projection data is within a reference to thereby determine the effective region of said projection angle from said region of reference error.

5. An X-ray CT image taking apparatus according to claim 1, wherein the judgment of the effective region of said projection angle is effected in parallel with said X-ray image taking, and if the effective region of said projection angle is less than an angle of a fan angle plus 180 degrees, said X-ray image taking is discontinued.

6. An X-ray CT image taking apparatus according to claim 1, wherein when said projection data overlaps in said effective region, the weight of the overlapping projection data is adjusted.

7. An X-ray CT image taking method of obtaining a reconstructed image from projection data obtained by X-ray image taking, provided with:

the calculating step of obtaining the degree of consistency of projection data opposite to the projection data of a projection angle at each projection angle;

the determining step of determining the effective region of said projection angle by the use of said degree of consistency obtained by said calculating step; and the tomographic image forming step of reconstructing an image by the use of said projection data in said effective region determined by said determining step to thereby obtain a tomographic image.

* * * * *

UNITED STATES PATENT AND TRADEMARK OFFICE
CERTIFICATE OF CORRECTION

PATENT NO. : 7,145,979 B2
APPLICATION NO. : 11/140898
DATED : December 5, 2006
INVENTOR(S) : Hiroyuki Urushiya It is certified that error appears in the above-identified patent and that said Letters Patent is hereby corrected as shown below:

ON THE TITLE PAGE [75]:

Inventors, "Saitama-ken" should read --Saitama--.

COLUMN 2:

Line 40, "an illustrate" should read --illustrate an--.

COLUMN 3:

Line 54, "greess" should read --degree--.

COLUMN 5:

Line 9, "$\delta+II$ to $\delta+\Delta\beta+II$." should read --$\gamma+II$ to $\gamma+\Delta\beta+II$.--; and
　　　Line 58, "reduceds" should read --reduces--.

Signed and Sealed this

Nineteenth Day of June, 2007

JON W. DUDAS
*Director of the United States Patent and Trademark Office*